(12) United States Patent
U et al.

(10) Patent No.: US 6,572,624 B2
(45) Date of Patent: Jun. 3, 2003

(54) STEREOTAXIC DETACHABLE NEEDLE EXTENSION

(76) Inventors: Hoi Sang U, P.O. Box 1003, Rancho Santa Fe, CA (US) 92067; James Peter Amis, 6740 Top Gun St., San Diego, CA (US) 92618

( * ) Notice: Subject to any disclaimer, the term of this patent is extended or adjusted under 35 U.S.C. 154(b) by 0 days.

(21) Appl. No.: 09/835,142

(22) Filed: Apr. 13, 2001

(65) Prior Publication Data

US 2002/0007187 A1 Jan. 17, 2002

Related U.S. Application Data

(60) Provisional application No. 60/196,618, filed on Apr. 13, 2000.

(51) Int. Cl.$^7$ ............................................ A61B 19/00
(52) U.S. Cl. ........................................................ 606/130
(58) Field of Search ................................. 606/130, 107; 600/429, 426, 411, 414, 417; 604/175

(56) References Cited

U.S. PATENT DOCUMENTS

| | | | | |
|---|---|---|---|---|
| 3,460,537 A | * | 8/1969 | Zeis | 606/130 |
| 4,826,487 A | * | 5/1989 | Winter | 604/175 |
| 5,595,193 A | * | 1/1997 | Walus et al. | 128/898 |
| 6,298,262 B1 | * | 10/2001 | Franck et al. | 600/426 |
| 6,331,180 B1 | * | 12/2001 | Cosman et al. | 606/130 |

* cited by examiner

*Primary Examiner*—Pedro Philogene
(74) *Attorney, Agent, or Firm*—Stout, Uka, Buyan & Mullins, LLP (57) ABSTRACT

An apparatus for positioning instrumentation into a target region of a brain generally includes an attachment member, specifically a disc adapted to be secured to a cranium, and a marker assembly adapted to be connected to a locator device, for example a conventional stereotaxic assembly. The marker assembly includes a detachable cannula, and is further adapted to be secured to the attachment member in order to immobilize the cannula at a precise position in the brain, thus facilitating additional imaging of the patient in order to determine the position of the cannula with respect to the target region.

59 Claims, 6 Drawing Sheets

STEREOTAXIC DETACHABLE NEEDLE EXTENSION

BACKGROUND OF THE INVENTION

1. Field of the Invention

The present invention relates generally to a stereotaxic surgical procedure and more specifically to a stereotaxic surgical procedure for the precise placement of an instrument to a specific target region in the brain.

2. Description of Related Art

Stereotaxic surgery has conventionally been the primary method for the precise placement of instruments to specific targets within the human brain. Despite its widespread use especially in the treatment of Parkinson's Disease, a certain margin of error in localization exists. This error may vary, for example, from 1 mm to 5 mm. Therefore, when precise localization is required, refinement of existing technology may be desired.

SUMMARY OF THE INVENTION

The present invention provides an apparatus and method for more accurately positioning instrumentation in a brain of a patient. The apparatus is straightforward in design and construction and can be used with existing technology without requiring a substantial level of increased surgical skill.

Accordingly, an apparatus for positioning instrumentation into a target region of a brain is provided, the apparatus generally comprising an attachment member adapted to be secured to a cranium of a patient and a marker assembly adapted to be connected to a locator device. The locator device may comprise, for example, a conventional stereotaxic headframe assembly, which is suitable for positioning an installation probe into a cranium of a patient based on predetermined coordinates derived, for example, from data obtained from a brain imaging scan.

In accordance with one aspect of the present invention the locator device includes a stereotaxic arc and an installation probe extending therefrom. The marker assembly generally comprises a cannula preferably made of a ceramic material. The cannula is adapted to fit over a distal portion of the installation probe such that a distal end of the cannula is closely, and preferably precisely, aligned with a distal end of the installation probe. The stereotaxic locator device is used to facilitate the insertion of the installation probe, having the cannula attached thereto, through a burr hole and into the brain such that the distal end of the installation probe and cannula are placed in close proximity of the target region to be treated. Upon being so positioned in the brain, a proximal end of the cannula is secured, preferably by an adhesive, to the attachment member in order to immobilize the cannula within the brain at the desired angular orientation.

Importantly, the marker assembly, including the cannula and a needle inserted through the cannula, is adapted to be detached and removed from the locator device after the cannula has been immobilized in the desired orientation. In one embodiment of the present invention, the needle is sized to extend at least about 5 mm to about 10 mm beyond the distal end of the cannula to the precise location of the target region. The needle preferably is formed of a carbon fiber, and may be constructed to include an indexing element or other means for determining and adjusting the effective depth of the needle into the brain in increments of less than about 5 mm, and more preferably in increments of about 1 mm or 2 mm. Advantageously, the marker assembly and attachment member have a sufficiently low surface profile, with respect to the cranium surface, to enable a surgeon to cover the wound with the scalp of the patient in order to maintain sterility of the surgical site.

The brain may then be subjected to a verification scan and imaging procedure, while the marker assembly is immobilized within the brain, in order to verify the position of the distal end of the needle with respect to the target region in the brain. Upon an optimal verification scan, the target region can then be treated by reopening the scalp and inserting a surgical device and/or treatment substance through the needle.

Notably, if the verification scan has revealed that the cannula is not at a desired orientation in the brain, the cannula and attachment member can be removed from the cranium and/or repositioned. Data and images obtained from the verification scan can be used in the calculation of new coordinates useful in the subsequent positioning of the same or another cannula.

The attachment member preferably comprises an Aluminum or other non-ferrous member, preferably a disc-shaped member including a flanged proximal portion circumscribing an aperture sized to receive the installation probe and marker assembly. Preferably, the flanged proximal portion has a diameter of between about 6 mm and about 16 mm, and has a radius of curvature approximating the radius of curvature of a human cranium. The attachment member further includes a substantially cylindrical distal protrusion depending from the flanged portion. The substantially cylindrical distal portion is adapted to fit within the burr hole, and to be at least partially filled with an adhesive for securing the cannula proximal end to the attachment member and hence to the cranium. The inner surface of the attachment member distal portion is textured or grooved, or may include one or more channels defining reservoirs for holding cured adhesive in place.

The attachment member is secured to the cranium by means of surgical screws or the like, with the flanged portion overlaying a periphery of the burr hole. Preferably, the attachment member has a depth that is less than a thickness of the cranium to which the attachment member is secured. The depth of the attachment member is preferably less than about 10 mm, for example about 6 mm, for a cranial plate having a thickness of about 10 mm. The attachment member is structured, when at least partially filled with cured adhesive, to immobilize the cannula when the installation probe is removed from within the cannula, the cannula being immobilized at the same orientation as the distal portion of the installation probe.

In accordance with one aspect of the present invention, a method for positioning instrumentation at an exact target region of a brain is provided. The method generally comprises the steps of securing an attachment member onto a cranium of a patient, connecting a marker assembly to a locator device, which is suitable for positioning the marker assembly in the brain based on predetermined location data of the target region, and introducing the marker assembly into the brain of the patient such that a distal tip of the marker assembly is located in a vicinity of the target region of the brain. Additional steps include immobilizing the marker assembly in the brain, and removing the locator device from the marker assembly while the marker assembly is immobilized in the brain. Preferably, the step of immobilizing the marker assembly includes a step of securing the marker assembly to the attachment member. In accordance with one aspect of the present invention, the method additionally includes a step of verifying the location of the marker assembly with respect to a location of the target region of the brain. Advantageously, the step of verifying can be performed while the marker device is immobilized within the brain and a determination can be made of whether the marker device is positioned accurately.

The step of verifying can include a step of obtaining data relating to the location of the marker assembly with respect to the location of the target region. In addition, the method preferably includes, after the step of verifying, a step of introducing a surgical instrument or active agent, such as a medication, through the needle of the marker assembly to treat the target region.

BRIEF DESCRIPTION OF THE DRAWINGS

The objects and advantages of the present invention will be more readily appreciated and understood with respect to the following Detailed Description, when considered in conjunction with the accompanying drawings of which:

FIGS. 6a–12 illustrate other embodiments of the present invention.

DETAILED DESCRIPTION OF THE PRESENTLY PREFERRED EMBODIMENTS

Figure 1:
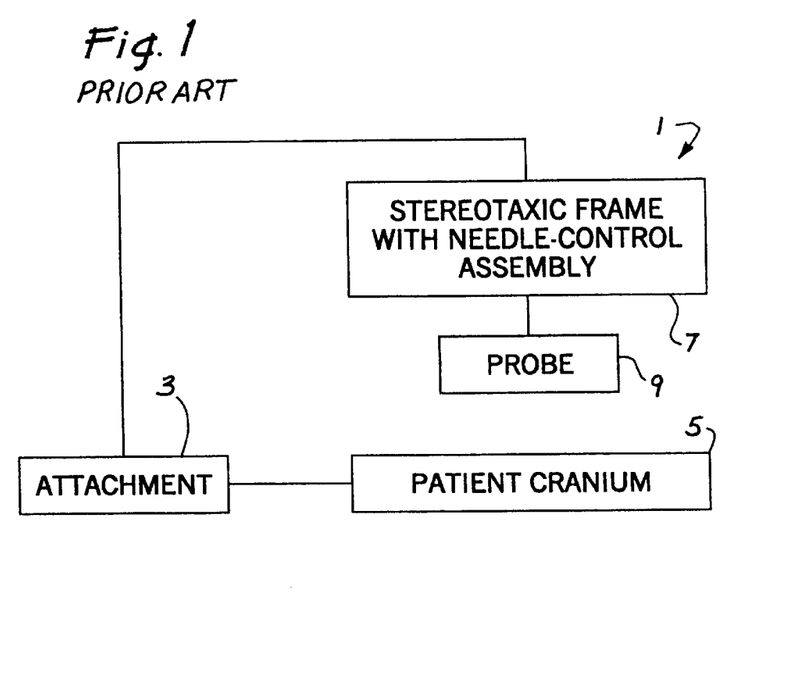
FIG. 1 illustrates a block diagram of a prior art apparatus for positioning instrumentation in a human brain.

Referring more particularly to the drawings, FIG. 1 illustrates a block diagram of a prior art apparatus 1a for positioning instrumentation in a cranium 5a of a patient. Particularly, in conventional stereotaxic surgical techniques, an attachment 3a is secured to the cranium 5a and a conventional locator device 7a is connected to the attachment 3a. A probe 9a is positioned above the cranium 5a and directed into an intra-cranial region of the cranium 5a, based on predetermined coordinates derived from earlier diagnostic analysis for example. The predetermined coordinates generally represent an approximation of a target location within the brain, for example, an area of brain tissue to be treated. Prior art analytical and medical instrumentation and procedures, which are suitable for stereotaxic surgery, are well known and for the sake of simplicity will not be detailed further herein.

Figure 2:
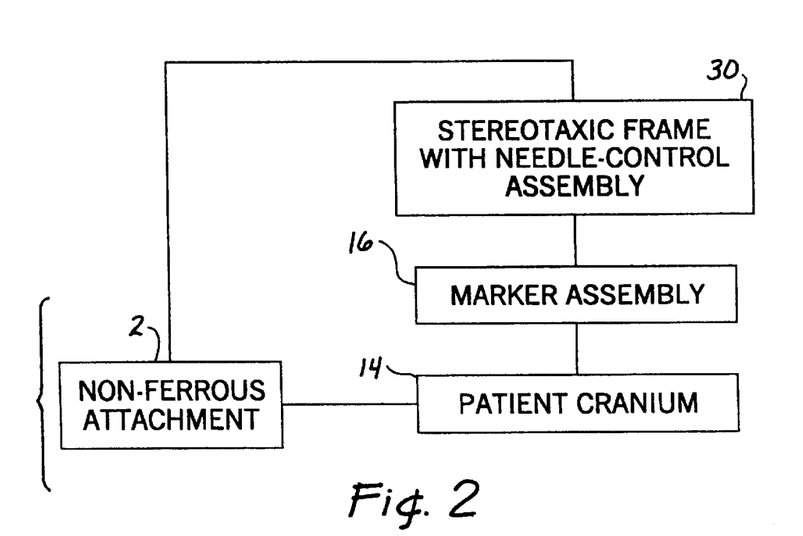
FIG. 2 illustrates a block diagram of a system in accordance with the present invention for positioning instrumentation in a human brain.
Figure 3:
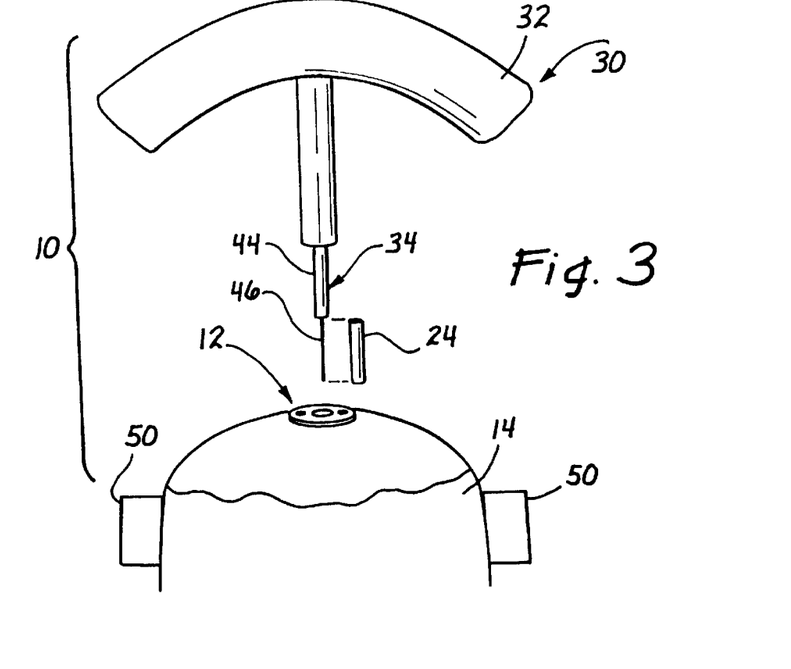
FIG. 3 illustrates a diagram of a system in accordance with the present invention, the system generally including an attachment member and a marker assembly adapted to be removably connected to a stereotaxic locator device.

A simplified block diagram of an apparatus 10 in accordance with the present invention, for more accurately positioning instrumentation into a target region of a brain, is illustrated in FIG. 2. The apparatus 10 comprises an attachment member 12, which is preferably constructed of an Aluminum or non-ferrous material and which is adapted to be secured to a cranium 14 of the patient. The apparatus 10 further comprises a marker assembly 16, which preferably includes a detachable member, such as a cannula 24 (FIG. 3). The detachable member is adapted to be connected to a locator device 30. The locator device 30 preferably comprises, for example, a conventional stereotaxic headframe assembly suitable for positioning a conventional probe within the brain based on predetermined location data, and further comprises an installation probe 34 (FIG. 3) for use in place of the conventional probe.

As will be described in greater detail hereinafter, the marker assembly 16 is adapted to be secured to the attachment member 12 and immobilized within the brain. The marker assembly 16 preferably comprises the cannula 24, which preferably comprises porcelain or ceramic and which is secured to the attachment member 12, and further comprises a needle 92 (FIG. 5), which preferably comprises a carbon fiber material and which is inserted through the cannula after the cannula is secured to the attachment member 12. The marker assembly 16 is adapted to be disconnected from the locator device 30 after being secured to the attachment member 12 and immobilized within the brain, wherein the marker assembly 16 remains immobilized and stationary during and subsequent to the process of being disconnected from the locator device 30.

This feature of the present invention allows for increased accuracy in the subsequent placement of the needle 92 by enabling additional scans, screenings or other diagnostic procedures to be performed on the patient, with the marker assembly 16 immobilized in place, prior to the patient undergoing subsequent treatment procedures. More specifically, high accuracy imaging techniques can be used to identify, for example, the location of the needle 92 relative to the target region of the brain. The present system 10 allows for correction, or refinement, of the placement of the needle 92 based on data obtained in the later verification procedures. Thus, once the marker assembly 16 is accurately placed, for example within about a 1 mm margin of error, for example, treatment of the target region can proceed.

Figure 4:
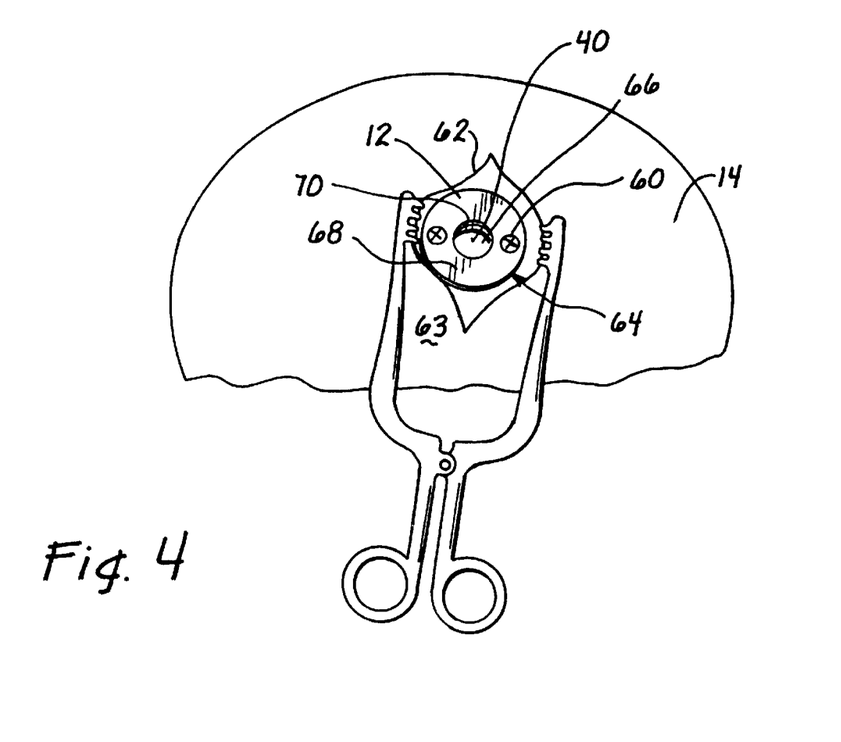
FIG. 4 illustrates a view of the attachment member in accordance with the present invention, secured by surgical bolts to a cranial plate during a stereotaxic surgical procedure.
Figure 5:
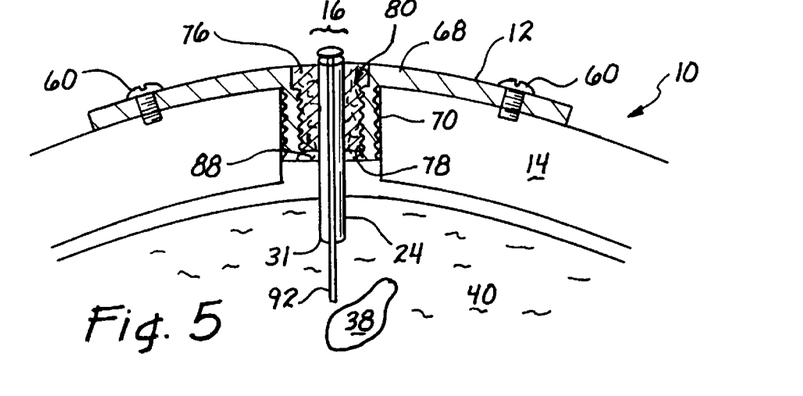
FIG. 5 illustrates a partial cross-sectional view of an apparatus of the present invention being used to locate and treat a target region in the brain.

Turning now to FIGS. 3–5, a preferred embodiment of the present invention is shown. The locator device 30 is illustrated comprising a stereotaxic arc 32 and the installation probe 34 extending therefrom. The installation probe 34 is adapted to extend from the stereotaxic arc 32 to a general vicinity of a target region 38 in the brain 40 (FIG. 5). More specifically, in accordance with the present invention, the installation probe 34 is configured to be accommodated at one end thereof by the conventional stereotaxic arc 32 and to accommodate at the other end the cannula 24. Referring now in particular to FIG. 3, it can be seen that, unlike a conventional stereotaxic probe (not shown), the installation probe 34 in accordance with the present invention is somewhat modified to include a proximal portion 44 and a distal portion 46, wherein the proximal portion 44 has a diameter larger than a diameter of the distal portion 46. The stereotaxic arc 32 is mounted to the patient cranium by means of a suitable mounting mechanism 50 in order to fix the locator device 30 with respect to the cranium 14.

The cannula 24 is adapted to fit over the distal portion 46 of the installation probe 34, preferably in frictional engagement therewith. The cannula 24 comprises an inner diameter which is about equal to the outer diameter of the distal portion 46 of the installation probe 34. The distal tip of the cannula 24, however, preferably comprises an inner diameter, which is slightly smaller than an inner diameter of the rest of the cannula 24, to thereby enable the cannula to frictionally engage and hold the installation probe 34. The cannula 24 can thus removably engage the distal portion 46 sufficiently securely to prevent the cannula 24 from detaching from the installation probe 34 under, for example, the pull of gravity. The cannula 24 can be readily detached from the installation probe 34 by a surgeon after the installation probe has been positioned in the brain 40 and secured to the attachment member 12. In a preferred embodiment of the present invention, an outer diameter of the cannula 24 is about equal to an outer diameter of the proximal portion 44 of the installation probe 34.

Turning now to FIG. 4, the attachment member 12 is illustrated secured by screws 60 or other fastening members directly to the cranium 14, after an incision 62 has been made in the scalp 63 of the patient. More specifically, the attachment member 12 is secured to an area of the cranium at a desired location determined to directly overlay the target region 38 in the brain. A location of the target region 38 (see FIG. 5) is predetermined by conventional imaging techniques, which are not described in detail herein.

In the presently preferred embodiment of the present invention, the attachment member 12 preferably comprises a disc 64 having an aperture 66 sized to receive the marker assembly 34, specifically, the detachable cannula 24 (see for example FIG. 5). More specifically, the disc 64 comprises a flanged proximal portion 68, hereinafter referred to as a flange or flanged portion. In the illustrated embodiment, the flanged portion 68 has a diameter of about 28 mm. The flanged portion 68 has a radius of curvature that approximates the radius of a human cranium such that the flange 68 lies substantially flat against the cranium. This feature provides a low profile and ensures that the disc 64 can be firmly fixed to the cranium and will remain secure and not become dislocated during the surgical procedure.

Turning now to FIG. 5, it is shown that the attachment member 12 is sized and configured to cover a portion of the cranium surface surrounding and extending into the burr hole. The disc 64 preferably includes a substantially cylindrical distal protrusion 70 extending substantially perpendicularly from the flanged portion 68. The distal protrusion 70 is sized to fit within a burr hole that has been created in the cranial plate, for example by conventional surgical techniques, in order to expose the outer dura of the brain 40. As presently preferred, the outer wall of the distal protrusion 70 should closely fit within the burr hole. In the illustrated embodiment, the burr hole has a diameter of about 14 mm and the maximum diameter of the distal protrusion is about 13 mm. The surgeon may choose from a selection of attachment members 12 in order to match the burr hole diameter, which may vary from, for example, 6 mm to about 16 mm.

The cannula 24 is adapted to be secured to the attachment member 12 and immobilized in a specific angular orientation within the brain 40. This specific orientation is, for example, an orientation in which the locator device 30 was used to position the cannula 24, when the cannula 24 was connected to the distal portion 46 of the installation probe 34 as described above. It is to be appreciated that although the cannula 24 is shown at a generally perpendicular orientation with respect to the cranium surface, the cannula 24 can be disposed in other desirable angular orientations as well.

After being positioned in the brain 40, the cannula 24 is firmly and rigidly secured to the attachment member disc 64 by means of an adhesive 80. By adhering the cannula 24 to the attachment member 12, the cannula is fixed and immobilized in a desired orientation within the brain 40 so that an axis of the cannula is calculated to intersect with the target region. As will be described hereinafter, the cannula 24 can than be detached from the locator device 30 by extracting the installation probe 34 from the cannula 24. The needle 92 can then inserted into the immobilized cannula 24 and used as a marker that can be imaged within the brain. Advantageously, the attachment member/cannula combination, i.e. the marker assembly 16, defines a low profile on the cranium surface. This facilitates a surgeon in performing additional scans, for example, verification scans, of the brain 40 without cumbersome and ferrous equipment being connected to the patient. The low profile also enables the surgeon to close the incision 62, maintaining a sterile environment, after removing the installation probe 34 and before performing a verification scan.

In the preferred embodiment shown, the distal protrusion 70 of the attachment member disc 68 defines a reservoir 76, including a grooved wall 78 for receiving the adhesive 80. In this preferred embodiment, the adhesive 80 comprises a catalyzing adhesive, for example a methyl methacrylate that will solidify in a short time period, for example a time period of less than 15 minutes.

Prior to introducing the adhesive 80, it is preferred that a medium is placed into the reservoir 76 between the grooved wall 78 and the cannula 24. In the presently preferred embodiment, the media comprises a commercially available resorbable gel foam 88 that is gently packed or positioned about the cannula 24 in order to prevent the fluid adhesive 80 from entering the cranial cavity. Suitable gel foam is typically provided in absorbable sheets of between about 3 mm and 6 mm in thickness. For use in the present invention, such a gel foam sheet is cut into small pieces and then hydrated, for example with a sterile saline solution which softens the pieces for insertion into the reservoir 76 of the distal protrusion 70. Although it is preferred that the distal protrusion 70 extend deep enough into the burr hole to provide for a great depth of adhesive for strong fixation of the cannula, it is also preferred that the distal protrusion not extend fully through the burr hole to protect the brain. The distal protrusion 70 is thus constructed in the illustrated embodiment to extend greater than half of the distance through burr hole but less than the full thickness of the cranium. In the illustrated embodiment, the burr hole is about 10 mm thick the distal protrusion extends about 6 mm therethrough, and the layer of gel foam 78 extends about1 mm to about 2 mm up from the bottom of the distal protrusion.

As shown, the adhesive-filled reservoir 76 at least partially circumscribes a proximal end 86 of the cannula 24 when the cannula 24 is secured to the attachment member 12 as illustrated in FIG. 5, and functions to secure the cannula 24 in a precise location within the brain 40. In other words, the reservoir 76 is structured, when at least partially filled with cured adhesive and when the installation probe 34 is removed from within the cannula 24, to immobilize the cannula 24 at the same orientation as the orientation of the distal portion of the installation probe at a time before the marker assembly 24 is disconnected from the locator device 30.

Still referring to FIG. 5, in a preferred embodiment of the present invention, the marker assembly 16 further comprises a needle 90, shown inserted through the immobilized cannula 24 such that a distal end 92 of the cannula 24 extends at least as far as the distal tip 31 of the cannula 24. In the illustrated embodiment, the needle 90 extends past the cannula distal tip 31 and marks the target region 38. The needle 90 preferably comprises a rigid, inflexible, high precision element, for example a carbon fiber, that does not scatter and provides high resolution under an imaging beam. The needle 90 preferably includes a lumen (not shown)

along a longitudinal axis thereof, through which an active agent, such as a medication can be directly delivered into brain tissue within the target area 38.

As mentioned, the distal protrusion 70 has a depth that is less than a depth of the cranium to which the attachment member 12 is secured. The depth of the attachment member is preferably less than about 10 mm. In addition, the flanged portion 68 will have a diameter that is partially dependent upon the diameter of the burr hole. In addition still, the radius of curvature of the flanged portion 68 will depend upon the radial curvature of the patient's cranium, which is known to vary depending upon the portion of the cranium to which the attachment member will be mounted. Thus, as previously mentioned, it will be appreciated that various sizes and curvatures of attachment members 12 may be made available to accommodate different situations.

In the preferred embodiment of the present invention, the marker assembly 16 is length adjustable. For example, the marker assembly 16 may comprise a plurality of needles, i.e. carbon fiber needles similar to needle 90, having different lengths. Preferably, each needle 90 comprises a proximal portion 98 with a diameter larger then a diameter of the lumen of the proximal end 86 of the cannula 24. Washers or other spacing means may be inserted between the proximal portion 98 and the cannula for providing high-precision spacing. Thus, a surgeon can choose a desired length of needle for treating the patient.

In accordance with the method of the presently preferred embodiment, a sterotaxic reference frame, such as the stereotaxic reference frame 50, is attached to the head of a patient via mounting plates 50, and as aperture or burr hole is generated in the cranium of the patient. The dura is also breached at the burr hole, to allow for settling of the brain. At this point, the attachment member 12 may be secured to the cranium 14, centered over the burr hole. Alternatively, the attachment number 12 may be secured at a later point in time.

After the brain has settled, the burr hole wound is closed, by suturing and/or bandaging thereof. The patient, with the stereotaxic reference frame attachment, is then transported to an imaging room in the hospital, for example. As presently preferred, a three-dimensional imaging marker assembly is then secured to the stereotaxic reference frame (e.g., mounting plates 50), and the patient's brain is imaged. The three-dimensional imaging assembly can then be removed, and the patient is brought back into the operating room. At this point, the burr hole wound is reopened, and if not already attached, the attachment member 12 is secured to the cranium 14. The stereotaxic arc 32 is then attached to the stereotaxic reference frame 50, and the imaging data is used to orientate and position the installation probe 34 for incision to the target region, based upon the imaging data obtained in the imaging scan of the patients brain.

At this or an earlier point, the cannula 24 is inserted over the distil portion 46 of the installation probe 34, and the resulting assembly is inserted into the patient's brain and into proximity of the desired target region of the patient's brain. As presently embodied, the installation probe 34 is inserted to a point just shy of the target region within the brain, so that the distil portion 46 and the cannula 24 do not actually extend fully to the target region. For example, the surgeon may determine to have the distil portion 46 of the installation probe 34, and the cannula 24, advanced to a point exactly 10 mm shy of the target region. Subsequently, when the needle 22 is inserted through the cannula 24, the needle 22 will be constructed to extend exactly 10 mm distally of the distil tip of the cannula 24, to thereby extend to the target region.

Once the installation probe 34, with the attached cannula 24, has been inserted to the desired location through the aperture of the attachment member 12, the method of the present invention performs steps to secure the cannula 24 to the attachment member 12 so that the cannula 24 is immobilized within the patient's brain for the subsequent removal of the installation probe 34. In the illustrated embodiment, pieces of hydrated gel foam 88 are carefully inserted through the aperture of the attachment member 12, distally into the protrusion portion 70. Care is of course taken not to bump or press against the cannula 24. The pieces of gel foam 88 preferably form a barrier at the distil end of the protrusion portion 70, so that an adhesive 80, preferably a catalyst and polymer adhesive, can be placed within the protrusion portion 70 with, for example, a syringe. The adhesive 80 preferably sets in about five to fifteen minutes, to thereby fix the orientation of the cannula 24 during and after the subsequent removable of the an installation probe 34.

In accordance with the method of the present invention, the installation probe 34 is subsequently withdrawn and the stereotaxic arc 32 removed. At this point, a needle 22 is selected to extend the proper distance beyond the cannula 24 to the target region. The proximal end of the needle 22 preferably comprises a head for abutting against the proximal end of the cannula 24 and, further, washers or other spacing means may be inserted between the proximal end of the needle and the proximal end of the cannula 24, for spacing versatility. Alternatively, a proximal portion of the needle 22 may be threaded, and a washer may be moved up and down the proximal threaded portion to adjust the length of the needle 22 that protrudes distally through the cannula 24.

Once the needle 22 has been carefully positioned within the cannula 24 to extend to the target region, the attachment member 12 can be covered with sutures and/or dressing, and the patient can be transported again to the imaging room for a verification imaging scan to ensure that the distil end of the needle 22 is indeed at the target region. If the verification scan provides data indicating that the needle 22 is on the mark, then the placement procedure is completed, and subsequent treatment procedures of the target region can be conducted. If, on the other hand, the verification scan shows the needle 22 to be off-target, then this data may be used to fine tune the placement of the needle 22. For example, another needle 22 maybe inserted to the proper depth and/or curved needles or memory-material needles maybe used alone or in combination with the needle 22, to reach the proper target region. Moreover, it may be prudent to remove the attachment member 12 and the associated cannula 24 and needle 24, so that the entire method may be repeated and concluded with a subsequent verification imaging scan. If the subsequent imaging yields the proper data, then the procedure may be concluded. If additional placement steps are needed, such as any of the above-discussed steps, then those steps can be conducted until proper placement is obtained.

Figure 6A:
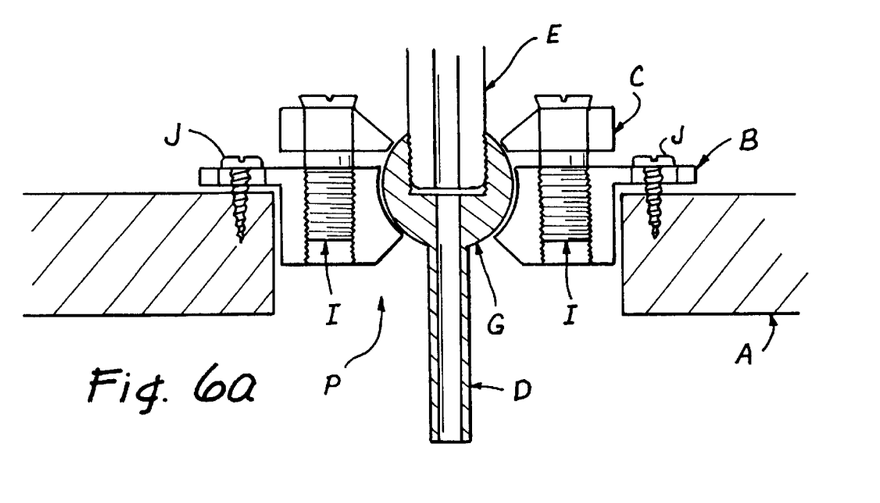
Figure 6B:
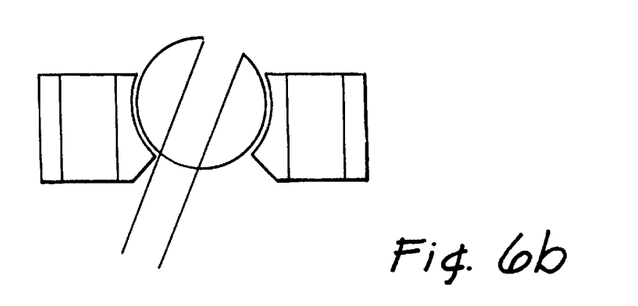

Other less preferred embodiments of the present invention are now described. Turning now to FIGS. 6a and 6b, one embodiment of the present invention is composed of a marker needle, which in turn is composed of two main parts, E and D. E and D correspond to the marker assembly 16. E and D can be securely locked to one another in a high-precision manner, for accurate positioning and alignment, via, for example, the sphere G. E and D can also be detached from each other. The sphere G is preferably integrally formed with D. In other embodiments, however, G has a different shape and/or is not integrally formed with D. The means through which E and D can be locked together can take the form of a thread and groove arrangement wherein a threaded cylindrical opening in G accommodates the distal threaded end of E. E is thus screwed into the sphere G of D for a precision-aligned and locked relationship. The upper end of E is precision secured to the installation probe of a conventional locator device 30 using high-precision hardware, e.g., a double-threaded sleeve, a sleeve with tightening screw, etc. Alternatively, the upper end of E is integrally formed with the installation probe. Any means known to those skilled in the art of fastening items, such as needles or other cannulated items, together may be used for either or both of the two cannula interfaces. The two cannula interfaces, i.e., the attachment of D to E and the attachment of E to the installation probe, may thus be secured in any known manner, so long as the attachment is accurate and stable enough for the intended purpose as set forth in this disclosure. For the double-threaded sleeve means of attaching E to the installation probe, for example, the distal tip of the installation probe will be formed with a thread suitable for being connected with a threaded end of the double-threaded sleeve. In another embodiment, this distal tip of the installation probe can be formed to screw directly into or around the proximal threaded end of E. A protrusion/indentation fitting may also be used to secure the distal tip of the installation probe to the proximal end of E. In embodiments wherein the distal tip of the installation probe is modified for accommodating a high-precision fit with the proximal end of E, a replacement installation probe may be substituted for the existing stereotaxic installation probe, wherein the replacement installation probe is formed with the modified distal tip. In other embodiments wherein a modified replacement installation probe is used, this needle may have E already connected, e.g., integrally formed, at the distal tip of the modified replacement needle. E and D are initially locked into each other. This sphere G in turn is enclosed at its circumference within two circular or otherwise shaped plates B and C. B and C are reversibly locked onto each other through the screws I. When the screws are tightened, C will be brought tightly onto B. This exerts pressure onto the outer circumference of sphere G fixing it in a specific position in relation to B and C.

During a stereotaxic procedure E is used to aim E and D in a specific direction toward the target region as determined by original scanning images. E and D are then lowered into the brain such that the tip of D is in the target region. There will be a number of D's such that the correct length can be chosen to reach each specific target in such a manner that B will be at the level of the outer table of the cranium A. During this part of the procedure, C is not tightened onto B. As a result, the C and B complex is loosely fitted around G and thus can be moved easily in relation to G. Once F reaches the target area and before C is tightly applied onto B such that B can still be moved in relation to G, B is secured onto the outer table of A using screws J.

Since C is not yet tightened onto B, the sphere G resides loosely in the C and B complex. Once B is securely fastened onto A, screws I are tightened thereby firmly fixing the sphere G in a specific relation to C and B. Since B is already firmly fixed onto A, the fixation of G onto C and B will result in G, D and E being fixed and maintained in a specific relation to A and the underlying brain. This will secure G and D in the target area in exactly the orientation determined by the stereotaxic coordinates. Alternatively, C may be secured to B via screws I and B subsequently secured to A via the screws J. In yet another alternative embodiment, C and/or B are secured to the non-ferrous attachment 10 instead of or in addition to the patient's cranium 12. Once D and G are secured onto A through B and C, E is detached from D and F and removed from the patient together with the stereotaxic frame with needle-control assembly 14. This allows G and D to be in the fixed position without a significant component such as E from protruding out of the cranium. The scalp can then be closed over C. The patient can then be moved to the scanner without the risks of contamination of the wound. A verification scan is then performed to determine the location of the tip of D and its relations to the target.

After the verification scan is performed, the patient is returned to the operating room where the scalp is sterilely prepped and the scalp reopened. The stereotaxic frame with installation probe is then reconnected to the cranium and E is reattached to G. B is detached from the cranium by removing screws J and C is loosened from B by loosening the screws I. If the aim of E and D is accurate, cannula and electrodes can be introduced to the target through the central opening in E and D. Should adjustments of the location of the tip of D be necessary, the coordinates of the tip of D as determined by the verification scan will be used as the reference. Repositioning of D can then be undertaken.

Figure 7:
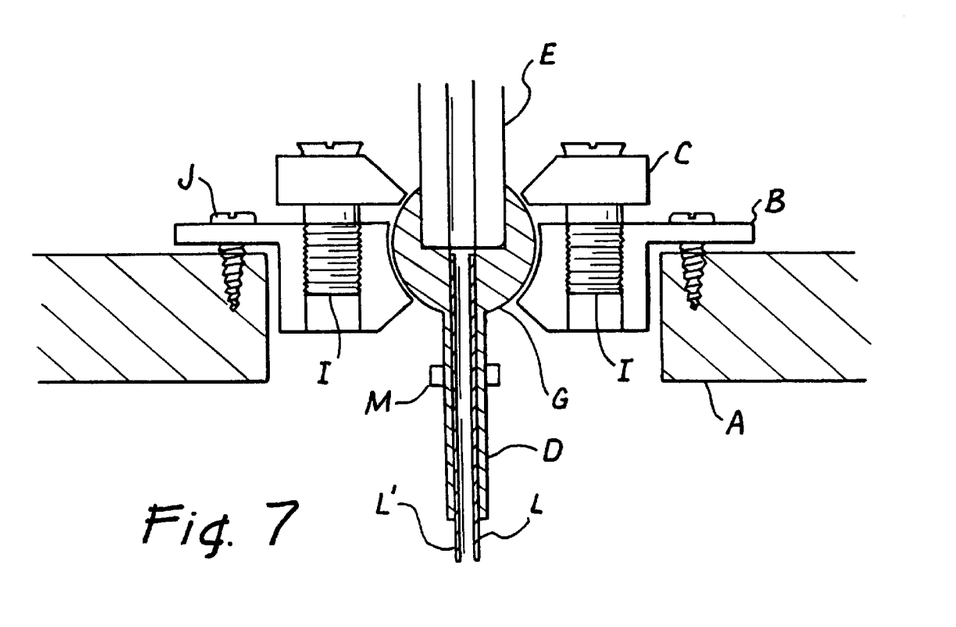

It was mentioned above that a number of D's will be present at the surgical procedure such that the correct length can be chosen to reach each specific target in such a manner that B will be at the level of the outer table of the cranium A. FIG. 7 illustrates another embodiment, where an inner cannula L is inserted into D to achieve a high precision fit within D. The dimensions of D and L are preferably selected so that the diameter of the lumen of L is equal to the diameter of the lumen of E.

In the embodiment of FIG. 4, the inventory of D's may be supplied at 5 mm increments. Thus, a surgeon in a procedure will determine the depth at which the target is beneath the outer table of the cranium and select the appropriate D accordingly. In this illustrative example, five inner cannulas L will be supplied at 1 mm increments to be used with the selected D to adjust the desired length to within 1 mm of the desired penetration length under the outer table of the cranium. In modified embodiments, the L's may be supplied at other incremental lengths such as, for example, 2 mm increments. The surgeon selects the desired L and fully inserts it into D until it reaches the end of the lumen within D (a ring-shaped stop, for example, denotes the end), and then tightens the washer M. Each L is preferably secured within D via a tapered washer M, which is screwed onto a tapered, threaded portion on the neck of D, for example, to clamp and hold the L. Any other high-precision structure may be provided to secure L within D to achieve a desired overall length. For example, one or more tightening screws may be used to engage L along its length within D, or any type of precision protrusion/indentation fitting may be used. In one embodiment, a single L is provided with indicia, such as "1 mm," "2 mm," etc. at its proximal end, to allow the user to precisely position L within D to achieve the desired extension length beyond the distal tip of D.

Figure 8:
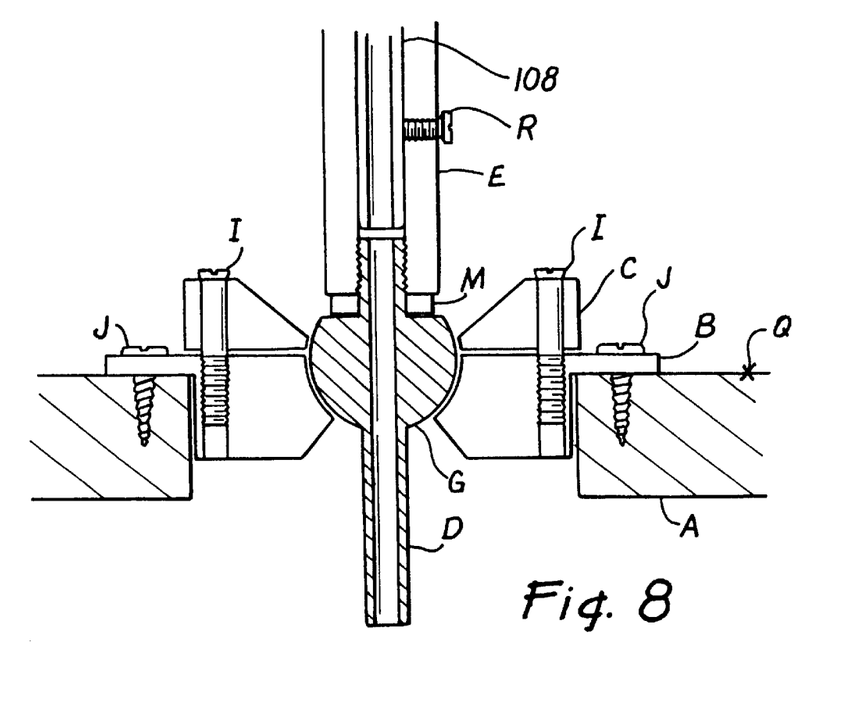

The embodiment of FIG. 8 is similar to that of FIG. 7, to the extent that an inner cannula L can be inserted into D to achieve a high precision fit within D. The dimensions of D and L are preferably selected so that the diameter of the lumen of L is equal to the diameter of the lumen of E. The diameter of the lumen of E is preferably equal to the lumen diameter of a stereotaxic installation probe needle. In other embodiments, however, the diameter of the lumen of L may be less than the diameter of the lumen of E. A surgeon in a procedure will determine the depth at which the target is beneath the outer table of the cranium and select the appropriate D accordingly. The inventory of D's may be supplied at 5 mm increments. In a modified embodiment, the inventory of D's may be supplied at 5 mm increments, in which case five inner cannulas L, for example, will be supplied at 1 mm increments to be used with the selected D. The net length can thus be adjusted to within 1 mm of the desired penetration length under the outer table of the cranium. In modified embodiments, the L's may be supplied at other incremental lengths such as, for example, 2 mm increments. The surgeon selects the desired L and fully inserts it into D until it reaches the ring-shaped stop denoting the end of the lumen within D, and then tightens the washer M. Each L is preferably secured within D via a tapered washer M, which is screwed onto a tapered, threaded portion on the neck of D, for example, to clamp and hold the L. Any other high-precision structure may be provided to secure L within D to achieve a desired overall length. For example, one or more tightening screws may be used to engage L along its length within D, or any type of precision protrusion/indentation fitting may be used. In one embodiment, a single L is provided with indicia, such as "1 mm," "2 mm," etc. at its proximal end, to allow the user to precisely position L within D to achieve the desired extension length beyond the distal tip of D.

Figure 9:
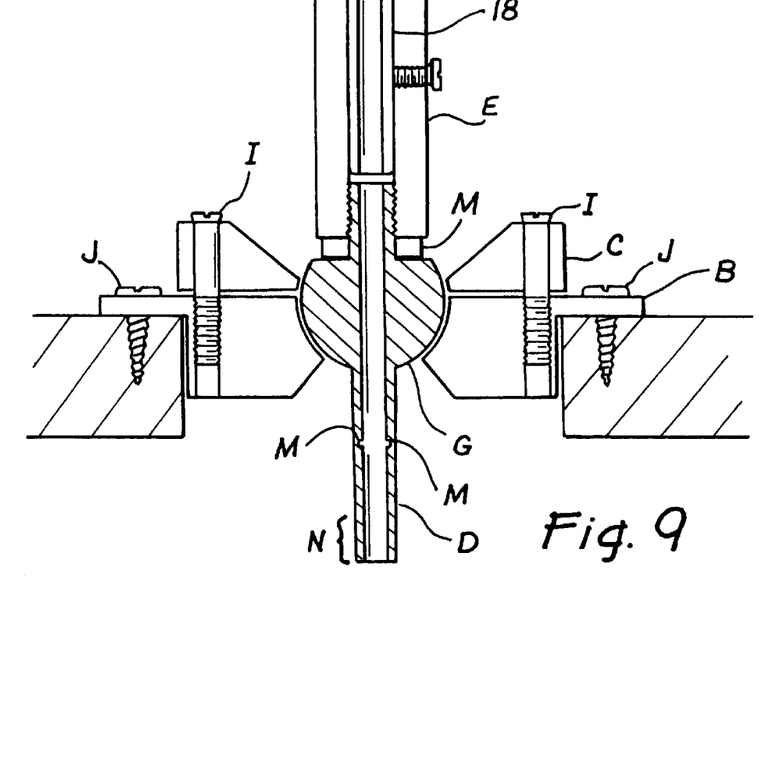
Figure 10:
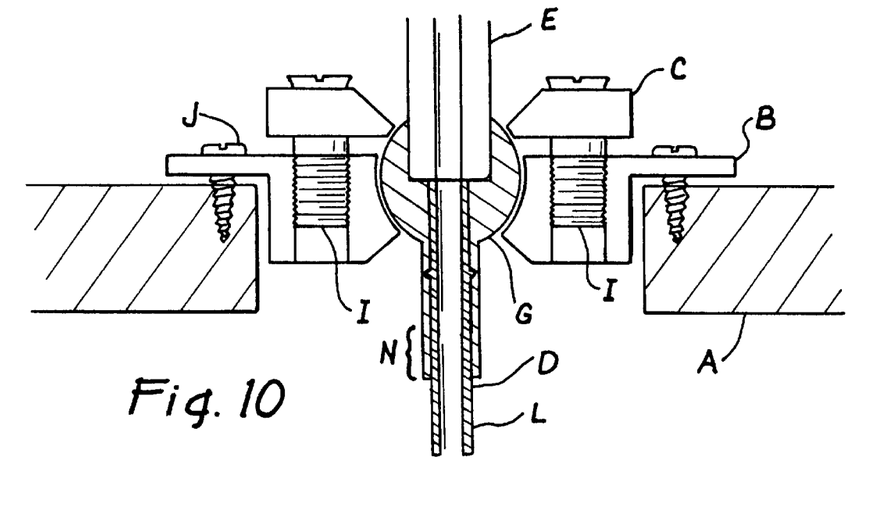
Figure 11:
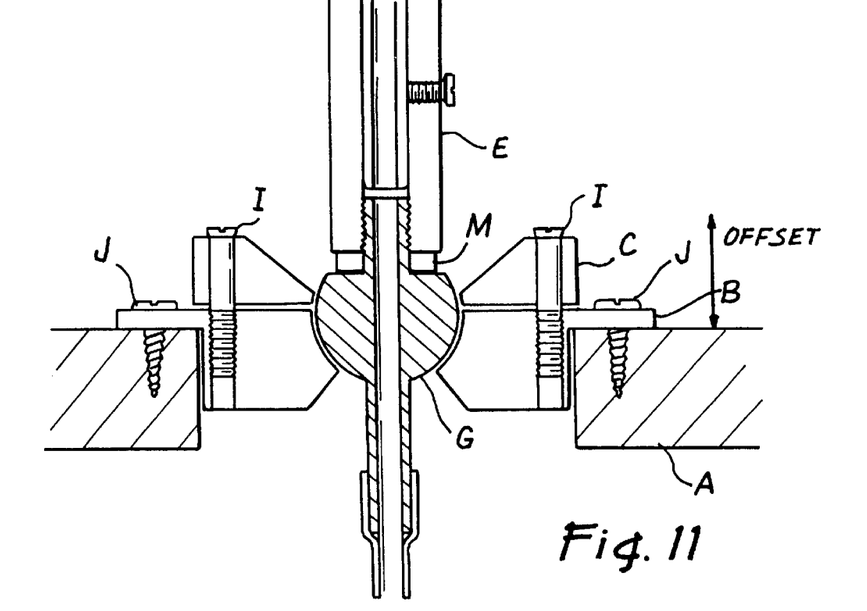
Figure 12:
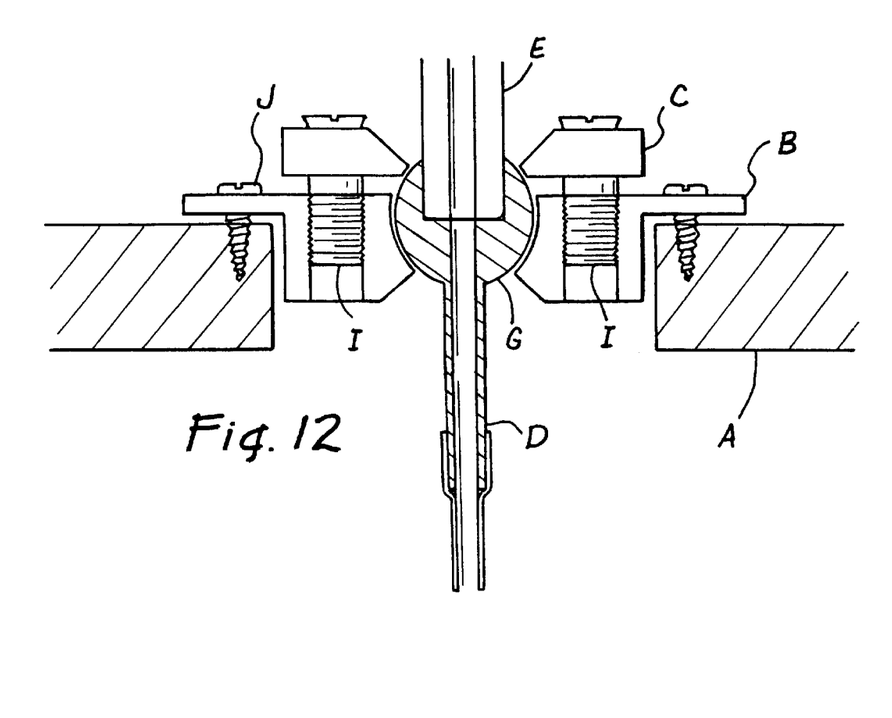

FIGS. 9 and 10 generally correspond to the embodiments of FIGS. 7 and 8, with the exception that a different construction is incorporated for holding the inner cannula (not shown). In FIG. 9, the outer diameter of the needle 117 is approximately equal to the inner diameter of G. Two indentations M are formed in D to accommodate complementary protrusions formed on the outer surface of the inner cannula. Longitudinal channels may be formed on the inner surface of the D for accommodating the protrusions on the inner cannula, and/or the indentations may comprise J channels for twist locking. Alternatively, threads may be formed at the interface of D and the inner cannula for a twist/lock fit. The threads would be formed on both surfaces at the area indicated by the letter N. The inner diameter of the needle 117 is preferably equal to that of the inner cannula, so that when the inner cannula is inserted into G the lumen bridging the needle 18 and the inner cannula is consistent in diameter throughout. FIG. 10 illustrates the same type of fitting between D and the inner cannula L, but shows a different configuration of E.

Each of the above features disclosed herein is included within the scope of the present invention, which as broadly defined herein comprises a detachable stereotaxic needle extension for facilitating a verification scan while the needle remains fixed at the target position. In addition all combinations of the presently disclosed features which are not mutually inconsistent or incompatible are also included within the scope of the present invention.

What is claimed is:

1. An apparatus for positioning instrumentation into a target region of a brain, the apparatus comprising:
   an attachment member adapted to be secured to a cranium of a patient; and
   a marker assembly adapted to be connected to a locator device, which is suitable for positioning the marker assembly within the brain based on predetermined location data of the target region, the marker assembly being adapted to be secured to the attachment member and immobilized within the brain;
   wherein the marker assembly is adapted to be disconnected from the locator device after being secured to the attachment member and immobilized within the brain, the marker assembly remaining immobilized and stationary while and after being disconnected from the locator device.

2. The apparatus of claim 1 wherein the locator device comprises a stereotaxic arc and an installation probe extending therefrom.

3. The apparatus of claim 2 wherein the installation probe is adapted to extend from the stereotaxic arc to a vicinity of the target region of the brain.

4. The apparatus of claim 3 wherein the marker assembly attaches to the locator device via the installation probe.

5. The apparatus of claim 4 wherein the installation probe includes a proximal portion and a distal portion, and the proximal portion has a diameter larger than a diameter of the distal portion.

6. The apparatus of claim 5 wherein the marker assembly comprises a cannula.

7. The apparatus of claim 6 wherein the cannula is adapted to be secured to the attachment member by means of an adhesive.

8. The apparatus of claim 7 wherein the attachment member includes a reservoir for receiving the adhesive, the reservoir at least partially circumscribing a proximal end of the cannula when the cannula is secured to the attachment member.

9. The apparatus of claim 8 wherein the reservoir is structured, when at least partially filled with cured adhesive and when the installation probe is removed from within the cannula, to immobilize the cannula at the same orientation as the orientation of the distal portion of the installation probe at a time before the marker assembly is disconnected from the locator device.

10. The apparatus of claim 9 wherein the marker assembly further comprises a needle adapted to be received in the cannula.

11. The apparatus of claim 10 wherein the cannula comprises a ceramic material and the needle comprises a carbon fiber.

12. The apparatus of claim 10 wherein the needle has a proximal end with a diameter larger then a diameter of a lumen of the cannula.

13. The apparatus of claim 6 wherein the installation probe of the locator device is adapted to be received in the cannula.

14. The apparatus of claim 6 wherein the cannula is sized to fit over the installation probe.

15. The apparatus of claim 14 wherein the cannula is frictionally engaged to the installation probe so that the cannula will not detach from the installation probe under the pull of gravity.

16. The apparatus of claim 10 wherein the needle within the cannula when the cannula is immobilized, extends to about the same location in the brain as the installation probe extended from the stereotaxic arc.

17. The apparatus of claim 1 wherein the marker assembly comprises a needle adapted to extend to about the target region of the brain when the marker assembly is immobilized in the brain.

18. The apparatus of claim 17 wherein the marker assembly further comprises a cannula adapted to be secured to the attachment member after being positioned in the brain by the locator device.

19. The apparatus of claim 18 wherein the cannula is adapted to receive the needle.

20. The apparatus of claim 19 wherein the needle has a proximal end with a diameter greater than a diameter of a lumen of the cannula.

21. The apparatus of claim 19 wherein the cannula is adapted to be secured to the attachment member by means of an adhesive.

22. The apparatus of claim 19 wherein the attachment member includes a reservoir for receiving the adhesive, the reservoir at least partially circumscribing a proximal end of the cannula.

23. The apparatus of claim 22 wherein the reservoir is structured, when at least partially filled with cured adhesive and when the installation probe is removed from within the cannula, to immobilize the cannula, the cannula being immobilized at the same orientation as the orientation of the distal portion of the installation probe.

24. The apparatus of claim 23 wherein the needle comprises a carbon fiber.

25. The apparatus of claim 18 wherein the locator device comprises a stereotaxic arc and an installation probe extending therefrom.

26. The apparatus of claim 25 wherein the installation probe is adapted to extend from the stereotaxic arc to a vicinity of the target region in the brain.

27. The apparatus of claim 26 wherein the marker assembly attaches to the locator device via the installation probe.

28. The apparatus of claim 27 wherein:
the installation probe includes a proximal portion and a distal portion, and the proximal portion has an outer diameter larger than an outer diameter of the distal portion;
the cannula has an inner diameter which is about equal to the outer diameter of a distal portion of the installation probe;
the cannula has a length about equal to a length of the distal portion of the installation probe; and
the cannula is adapted to frictionally engage the distal portion of the installation probe.

29. The apparatus of claim 28 wherein the installation probe comprises a carbon fiber.

30. The apparatus of claim 5 wherein the marker assembly is length adjustable.

31. The apparatus of claim 30 wherein the marker assembly comprises a plurality of needles having different lengths, each needle comprising a proximal portion with a diameter larger then a diameter of a lumen of a proximal end of the cannula.

32. The apparatus of claim 31 wherein the attachment member comprises a disc having an aperture sized to receive the marker assembly.

33. The apparatus of claim 32 wherein the proximal end of the cannula is adapted to be firmly and rigidly secured to the attachment member by an adhesive.

34. The apparatus of claim 33 wherein the attachment member includes a reservoir for receiving the adhesive, the reservoir at least partially circumscribing the proximal end of the cannula.

35. The apparatus of claim 34 wherein the reservoir is structured, when at least partially filled with cured adhesive, to immobilize the cannula at the same orientation as an orientation of the distal portion of the installation probe.

36. The apparatus of claim 32 wherein the attachment member includes a flanged proximal portion.

37. The apparatus of claim 36 wherein the flanged proximal portion has a diameter of between about 6 mm to about 16 mm.

38. The apparatus of claim 36 wherein the flange of the attachment member has a radius of curvature approximating the radius of curvature of a human cranium.

39. The apparatus of claim 38 wherein the attachment member further includes a substantially cylindrical distal protrusion extending substantially perpendicularly from the flanged portion.

40. The apparatus of claim 39 wherein the substantially cylindrical distal protrusion comprises a grooved wall for receiving an adhesive.

41. The apparatus of claim 39 wherein the substantially cylindrical distal protrusion has a depth that is less than a depth of the cranium to which the attachment member is secured.

42. The apparatus of claim 41 wherein the depth of the attachment member is less than about 10 mm.

43. The apparatus of claim 1 wherein the marker assembly is sized sufficiently small to enable a scalp of the patient to be closed over the marker assembly when the locator device is removed from the marker assembly and the marker assembly is immobilized in the brain.

44. A method for positioning instrumentation into a target region of a brain, the method comprising the following steps:
securing an attachment member onto a cranium of a patient;
connecting a marker assembly to a locator device, which is suitable for positioning the marker assembly in the brain based on predetermined location data of the target region;
introducing the marker assembly into the brain of the patient such that a distal tip of the marker assembly is located in a vicinity of the target region of the brain;
immobilizing the marker assembly in the brain; and
removing the locator device from the marker assembly while the marker assembly is immobilized in the brain.

45. The method of claim 44 wherein the locator device comprises an installation probe.

46. The method of claim 44 wherein the step of immobilizing includes a step of securing the marker assembly to the attachment member.

47. The method of claim 46 further comprising a step of verifying the location of the marker assembly with respect to a location of the target region of the brain.

48. The method of claim 47 wherein the step of removing the locator device is performed before the step of verifying.

49. The method of claim 44 wherein the step of removing includes a step of removing an installation probe of the locator device from the brain.

50. The method of claim 49 further comprising, after the step of removing the installation probe, a step of verifying the location of the marker assembly immobilized in the brain with respect to a location of the target region of the brain.

51. The method of claim 50 wherein the step of verifying includes the step of obtaining data relating to the location of the marker assembly with respect to the location of the target region.

52. The method of claim 51 wherein the step of verifying is followed by steps of removing the cannula and repositioning the cannula in the brain based upon data obtained in the verification step.

53. The method of claim 51 further comprising a step of introducing a needle into the marker assembly before the step of verifying.

54. The method of claim 53 wherein the cannula is secured to the attachment member with an adhesive.

55. The method of claim 53 wherein the step of introducing a needle comprises introducing a needle to a depth of the brain based on the predetermined data of the target region.

56. The method of claim 55 further comprising a step of treating the target region of the brain with the needle introduced therein.

57. The method of claim 56 wherein the step of treating includes introducing an active agent through the needle and into the brain.

58. The method of claim 44 further comprising a step of allowing the brain to settle after the step of securing the attachment member and before the step introducing the marker assembly.

59. The method of claim 44 further comprising a step of substantially closing the scalp of the patient over the marker assembly after removal of the locator device.

* * * * *